United States Patent [19]

Baylis et al.

[11] 4,099,518
[45] Jul. 11, 1978

[54] BIOPSY APPARATUS

[76] Inventors: Shelby M. Baylis, 1761 Schoenith, Bloomfield Hills, Mich. 48013; Jorge S. Szauer, 142 S. Johnson, Pontiac, Mich. 48053

[21] Appl. No.: 684,480

[22] Filed: May 10, 1976

[51] Int. Cl.² .................................................. A61B 10/00
[52] U.S. Cl. ............................ 128/2 B; 30/113.1; 128/310; 128/347
[58] Field of Search .............. 128/2 B, 310, 347, 304, 128/355, 314; 30/113.1, 113.2, 130, 316

[56] References Cited

U.S. PATENT DOCUMENTS

| | | | |
|---|---|---|---|
| 2,919,692 | 1/1960 | Ackermann | 128/2 B |
| 3,175,554 | 3/1965 | Stewart | 128/2 B |
| 3,512,519 | 5/1970 | Hall | 128/2 B |
| 3,683,891 | 8/1972 | Eskridge et al. | 30/113.1 X |
| 3,949,747 | 4/1976 | Hevesy | 128/2 B |

Primary Examiner—Robert W. Michell
Assistant Examiner—Michael H. Thaler
Attorney, Agent, or Firm—Irving M. Weiner

[57] ABSTRACT

An improved biopsy apparatus is disclosed. The apparatus comprises a hollow outer cannula within which is initially disposed a solid inner puncture trocar. In use, a biopsy sample is obtained from a patient by first inserting the outer cannula - trocar apparatus into the patient to a desired location. Thereafter, the solid inner initial puncture trocar is withdrawn from the outer cannula, while the other cannula remains in place at the desired specimen location. A hollow inner cannula is then inserted into the outer cannula, and upon withdrawal of the inner cannula from the outer cannula the desired specimen is obtained within the hollow interior of the inner cannula.

5 Claims, 7 Drawing Figures

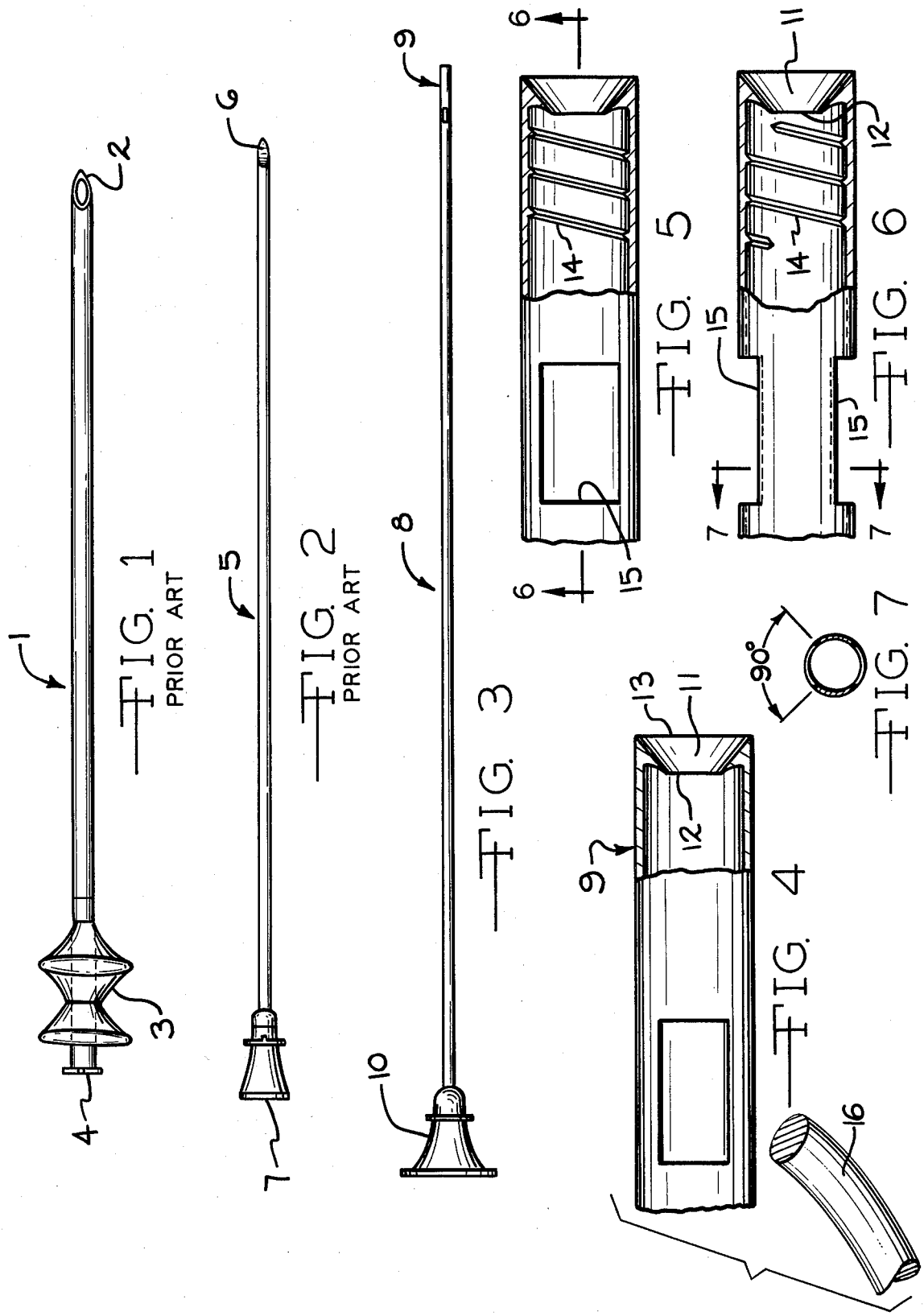

BIOPSY APPARATUS

BACKGROUND OF THE INVENTION

1. Field of the Invention

The present invention relates generally to an apparatus for use in connection with obtaining biopsy specimens such as, for example, from the breast, thyroid, solid tumors, bone marrow, liver, kidney, pleura, synovia, and other soft tissue.

2. Description of the Prior Art

Heretofore, there has not been developed any generally acceptable and workable biopsy device which lends itself to neatly and relatively painlessly removing a biopsy tissue sample from a patient and at the same time providing easy removability of the specimen from the device without endangering the patient or the quality of the extracted specimen.

Among the biopsy devices disclosed to date are those described in U.S. Pat. Nos. 2,541,542; 3,628,524; 3,800,783; 3,893,445; and 3,913,566. Such prior art devices have employed methods for extracting specimens such as, for example, by means of rotation of a needle device, by means of a loop of cutting thread disposed on a cannula, by means of a hooked blade arranged within a removable specimen gathering sheath, or by means of a cutting tube disposed within a hollow handle, amongst other things. Such devices, however, have not satisfactorily met the demand for a safe biopsy instrument which is capable of producing satisfactory specimens.

The present invention eliminates the disadvantages and shortcomings attendant all of these conventional prior art devices by providing a biopsy apparatus having an improved construction to reduce trauma to the patient and to provide a high quality tissue specimen without endangering either the patient or the extracted specimen.

SUMMARY OF THE INVENTION

The present invention provides an apparatus for extracting biopsy samples and the like. The apparatus includes an elongated hollow outer cannula having open distal and proximal ends, the distal end defining a cutting edge. Solid inner means corresponding generally in length and shape to the outer cannula is provided which is adapted to be tightly received within the hollow outer cannula for initial penetration of the body tissue. A hollow inner cannula adapted to be received within the hollow outer cannula after the solid initial puncture means has been removed therefrom is also provided, and the inner cannula has an elongated distal cutting end section which projects beyond the distal cutting edge of the outer cannula when the inner cannula is introduced thereinto in operative position. Also, the distal cutting end section of the inner cannula has disposed therein cutting means for cutting the body tissue as the inner cannula is withdrawn from the body and thus causing the tissue sample to be collected interiorly of the hollow inner cannula.

It is an object of the present invention to provide a biopsy apparatus having three main elements including a hollow outer cannula having disposed therein either a solid inner initial puncture trocar or a hollow inner cannula.

In accordance with a preferred embodiment of the present invention, the hollow inner cannula is provided with a novel distal cutting end section having disposed therein a truncated conical cutting section having its base adjacent the distal edge of the inner cannula so as to effect a specimen-cutting action upon withdrawal of the inner cannula from the patient's body. Optionally, there may be provided at least one sharp thread on the inner periphery of the novel inner cannula end section.

Another object of the invention is to provide a biopsy apparatus wherein the novel cutting end section of the inner cannula is provided with a through hole to facilitate removal of an extracted specimen from the interior of the inner cannula and means are provided for inserting into the through hole to remove the specimen.

Further objects and details of the present invention will become apparent to those skilled in the art upon reading the following specification, appended claims and the accompanying drawing.

BRIEF DESCRIPTION OF THE DRAWINGS

FIG. 1 illustrates a side elevational view of a prior art hollow outer cannula.

FIG. 2 depicts a side elevational view of a prior art solid inner puncture trocar.

FIG. 3 illustrates a side elevational view of a hollow inner cannula with novel end section in accordance with the present invention.

FIG. 4 depicts an enlarged sectional view of the novel end section shown in FIG. 3 in accordance with a first embodiment of the invention.

FIG. 5 illustrates an enlarged sectional view of the novel end section shown in FIG. 3 in accordance with a second embodiment of the invention.

FIG. 6 depicts a view of the novel end section taken along line 6—6 of FIG. 5.

FIG. 7 illustrates a view of the novel end section taken along the line 7—7 in FIG. 6.

DETAILED DESCRIPTION OF THE INVENTION

With reference to FIG. 1, there is shown a hollow outer cannula of conventional construction. The cannula 1 includes a beveled distal end point 2 for penetration into the body tissue and a hub 3 of standard construction to permit gripping of the hub in the fingers of the user. Both the beveled distal end point 2 and the proximal end 4 of the cannula 1 are open.

FIG. 2 illustrates a solid inner initial puncture trocar 5 which is also of standard construction. The trocar 5 corresponds generally in length and shape to the cannula 1 so as to fit snugly therein. The beveled distal end 6 of the trocar 5 is designed to match the beveled distal end 2 of the cannula 1. Upon insertion of the trocar 5 into the cannula 1, the respective beveled distal ends of the cannula 1 and trocar 5 will align with each other and the hub portion 7 of the trocar 5 will extend beyond the open proximal end 4 of the cannula 1 to permit easy extraction of the trocar 5 from the cannula 1.

Referring now to FIG. 3, there is shown a hollow inner cannula 8 having a novel end section designated generally as 9. The inner cannula 8 corresponds generally in shape to the outer cannula 1, and will thus also fit quite snugly into the outer cannula 1. Upon insertion of the inner cannula 8 into the outer cannula 1, the novel end section 9 of inner cannula 8 will extend approximately 3 cm beyond the open distal end 2 of the outer cannula 1, and the hub portion 10 of inner cannula 8 will extend sufficiently beyond open end 4 of outer cannula 1 so as to permit easy maneuvering of the inner cannula 8 within the outer cannula 1.

It should be noted that the outer cannula 1, the inner trocar 5 and the inner cannula 8 may be constructed of standard materials commonly used in the manufacture of surgical instruments. For example, stainless steel, polyurethane, or other suitable surgical material may be employed.

In operation, the trocar 5 is first inserted into the hollow outer cannula 1. The trocar-cannula apparatus is next inserted into the patient's body at the desired specimen extracting location. The beveled end 2 of outer cannula 1 having the beveled end 6 of trocar 5 aligned therein thus serves to penetrate the body tissue. The solid inner trocar 5 serves as a guide for the outer cannula 1 during insertion and also prevents body tissue from entering the hollow outer cannula 1. After full insertion, the trocar 5 is withdrawn completely from the outer cannula 1 while the outer cannula 1 remains stationary in the patient's body.

Next, the inner cannula 8 is completely inserted into the outer cannula 1 so that the novel end section 9 extends approximately 3 cm beyond the open distal end 2 of outer cannula 1. The end section 9 of inner cannula 8 may preferably have disposed therein a truncated conical cutting section 11 having its base adjacent the distal edge 13 of the inner cannula 8, as depicted in FIG. 4. The conical cutting section 11 performs a cutting action by means of its sharp truncated edge 12. Preferably, the angular space formed between the conical cutting section 11 and the interior of the end section 9 is at least partially solid so as to prevent the specimen from becoming trapped therein. It can thus be seen that when the inner cannula 8 is withdrawn from the patient's body, the truncated edge 12 of the conical cutting section 11 will perform a cutting action and cause body tissue to accumulate interiorly of the end section 9 during the withdrawal operation. It should be noted that the outer cannula 1 and inner cannula 8 are preferably withdrawn simultaneously from the patient's body. The specimen collected interiorly of the end section 9 will be approximately 2.5 cm to 3 cm in length, due to the 3 cm length of end section 9 which protrudes beyond distal end 2 of outer cannula 1.

Referring now to FIG. 5, there is illustrated a second embodiment of the novel end section 9 of inner cannula 8. In addition to the truncated conical cutting section 11, the interior surface of the end section 9 is further provided with sharp cutting threads 14. The cutting threads 14 are shaped in a manner so as to aid the truncated conical cutting section 11 in cutting and retaining the body tissue interiorly of the end section 9 upon withdrawal thereof from the patient's body. With the provision of cutting threads 14, and also in any desired application of the invention, it is beneficial to rotate the inner cannula 8 before withdrawal from the patient's body, while the outer cannula 1 remains stationary. Such rotating action will not be traumatic to the patient since the outer cannula 1 remains stationary, and will serve to aid in the cutting action performed by the cutting means of end section 9.

As depicted in FIGS. 4, 5 and 6, the novel end section 9 of inner cannula 8 is provided with a through hole 15. After the inner cannula 8 and the outer cannula 1 have been simultaneously withdrawn from the patient's body, the inner cannula 8 is thereafter entirely withdrawn from the outer cannula 1. The extracted specimen which is contained interiorly of the end section 9 is thereafter easily removed from the end section 9 via the through hole 15. This can be performed, for example, by inserting a wire 16 (FIG. 4) or other suitable implement into the through hole 15 to aid in extracting the specimen therefrom. As shown in FIG. 7, the through hole preferably consumes 90° of either side of the cylindrical periphery of the end section 9.

It will of course be understood that various changes may be made in the details, arrangement and proportions of the various parts without departing from the scope of the invention. The present embodiments are therefore to be considered as illustrative, and not restrictive. The scope of the invention is indicated by the appended claims rather than by the foregoing description, and all changes which come within the meaning and range of equivalency of the appended claims are therefore intended to be embraced therein.

We claim:

1. An apparatus for extracting biopsy samples and the like, comprising, in combination:
   an elongated hollow outer cannula having open distal and proximal ends, said distal end defining a cutting edge;
   solid inner means corresponding generally in length and shape to said outer cannula and being adapted to be tightly received within said hollow outer cannula for initial penetration of the body tissue;
   a hollow inner cannula adapted to be received within said hollow outer cannula after said solid initial puncture means has been removed therefrom;
   said inner cannula having an elongated distal cutting end section which projects beyond the distal cutting edge of said outer cannula when said inner cannula is introduced thereinto in operative position;
   said distal cutting end section of said inner cannula having disposed therein cutting means for cutting the body tissue as the inner cannula is withdrawn from the body and thus causing the tissue sample to be collected interiorly of the hollow inner cannula;
   said distal cutting end section of said inner cannula being provided with a through hole to facilitate removal of an extracted specimen from the interior of said inner cannula;
   means being provided for inserting into said through hole to remove the specimen;
   said cutting means disposed within said distal cutting end section of said inner cannula including a truncated conical cutting section having its base adjacent the distal edge of said inner cannula; and
   at least one sharp thread disposed on the inner periphery of said cutting end section to effect a tissue-cutting action when said inner cannula is rotated.

2. The apparatus as defined in claim 1, wherein:
   the angular space formed between said truncated conical cutting section and the interior surface of said end section is at least partially solid; and
   said inner initial puncture means comprises a trocar.

3. The apparatus as defined in claim 1, wherein:
   said distal cutting end section of said inner cannula is provided with a through hole to facilitate removal of an extracted specimen from the interior of said inner cannula; and
   means are provided for inserting into said through hole to remove the specimen.

4. The apparatus as defined in claim 3, wherein:
   said through hole embraces approximately 90° of the cylindrical periphery of said inner cannula.

5. An apparatus for extracting biopsy samples and the like, comprising, in combination:

an elongated hollow outer cannula having open distal and proximal ends, said distal end defining a cutting edge;

solid inner means corresponding generally in length and shape to said outer cannula and being adapted to be tightly received within said hollow outer cannula for initial penetration of the body tissue;

a hollow inner cannula adapted to be received within said hollow outer cannula after said solid initial puncture means has been removed therefrom;

said inner cannula having an integral cylindrical elongated distal cutting end section which projects beyond the distal cutting edge of said outer cannula when said inner cannula is introduced thereinto in operative position;

said distal cutting end section of said inner cannula having disposed therein cutting means for cutting the body tissue as the inner cannula is withdrawn from the body and thus causing the tissue sample to be collected interiorly of the hollow inner cannula;

said cutting means disposed within said distal cutting end section of said inner cannula including a truncated conical cutting section having its base adjacent the distal edge of said inner cannula; and at least one sharp thread disposed on the inner periphery of said cutting end section to effect a tissue-cutting action when said inner cannula is rotated.

* * * * *